United States Patent [19]

Asmussen et al.

[11] Patent Number: 4,593,054

[45] Date of Patent: Jun. 3, 1986

[54] ADHESION PROMOTING AGENT, PROCESS FOR ITS PREPARATION AND USE THEREOF ON COLLAGENEOUS MATERIAL

[75] Inventors: Erik Asmussen, Farum; Christian Munksgaard, Kokkedal, both of Denmark

[73] Assignee: Bayer Aktiengesellschaft, Leverkusen, Fed. Rep. of Germany

[21] Appl. No.: 765,032

[22] Filed: Aug. 12, 1985

Related U.S. Application Data

[63] Continuation of Ser. No. 664,117, Oct. 23, 1984.

[30] Foreign Application Priority Data

Oct. 25, 1983 [DK] Denmark .............................. 4898/83

[51] Int. Cl.$^4$ .............................................. C08K 5/07
[52] U.S. Cl. .................. 523/118; 433/228.1; 523/120
[58] Field of Search ................ 523/116, 118, 120; 433/228.1

[56] References Cited

U.S. PATENT DOCUMENTS

| | | | |
|---|---|---|---|
| 2,721,879 | 10/1955 | Popkin | 526/208 |
| 2,891,037 | 6/1959 | Reinhard | 526/315 |
| 3,154,599 | 10/1964 | Wismer | 526/315 |
| 3,310,531 | 3/1967 | Ryder | 526/208 |
| 3,448,069 | 6/1969 | Brown | 526/315 |
| 4,016,127 | 4/1977 | Lapsson | 526/315 |
| 4,315,089 | 2/1982 | Naarmann | 526/315 |

*Primary Examiner*—Paul R. Michl
*Attorney, Agent, or Firm*—Sprung, Horn, Kramer & Woods

[57] ABSTRACT

A primer composition for providing bonding between collagen containing materials, including dentin, bones and leather, and acrylate resins is disclosed comprising a monomer of the acrylate type containing reactive hydrogen and an aldehyde group containing compound. The combination may be made as a physical mixture or a chemical reaction product.

6 Claims, No Drawings

ADHESION PROMOTING AGENT, PROCESS FOR ITS PREPARATION AND USE THEREOF ON COLLAGENEOUS MATERIAL

This is a continuation of application Ser. No. 664,117, filed Oct. 23, 1984.

The present invention relates to an adhesion promoting agent (which is a primer, liner, or varnish composition), preferably for collagen containing materials, especially dentin, bones and leather, for application in aqueous environments before treatment with a setting composition based on an olefinically unsaturated monomer, preferably a (meth)acrylate. The adhesion promoting agent comprises a composition consisting of an aldehyde and a (meth)acrylate acid ester and preferably water.

The primer or liner composition of the invention is especially suitable for use within dentistry where for long time there has been a need for better adhesion of acrylate or methacrylate based composite resins used for dental filling and repair, such resins having the disadvantage of poor bonding to dentin. Thus, the technique of undercutting for better retention of fillings has been used, which, however, requires removal of considerable amounts of healthy dentin beyond the decayed region. Another procedure involves etching both dentin and enamel surfaces with acids, particularly phosphoric acid. Apart from the irritating effect on the gingiva, acids tend to penetrate the dentinal tubuli and to hurt the pulp. Practitioners, therefore, are reluctant to make use of such acidic treatments, which, nevertheless, have been found to increase the bonding, especially to enamel surfaces, of the known types of resin fillings.

European Patent Application No. 0058483 discloses dentin and enamel adhesives based on organic esters of phosphoric acids wherein chlorine or bromine is linked directly to phosphor. Accordingly, a polymerizable monomer, preferably Bis-GMA (a glycidyl methacrylate of bisphenol A), is reacted with the phosphorous containing acid or phosphoroxychloride ($POCl_3$). The resulting product forms part of a two-component composition, the other component of which may e.g. be an ethanolic solution of sodium benzene sulphonate and DHPT (N,N-dihydroxyethyl-p-toluidine).

This composition has an improved adhesive effect when the tooth after drilling, rinsing with water and blowing dry with air has been etched. The above first component of the composition may be replaced by a reaction product of phosphoroxychloride and e.g. 2-hydroxy ethylmethacrylate. If a cavity in the tooth is then filled with a usual dental filling composition based on (meth)acrylates, however, on unetched dentin, only poor bonding strength is obtained, which is substantially lower than the best results obtained with etched enamel (at most only 1/10 of the bonding strength on etched dentin).

Moreover, the conventional (meth)acrylate filling compositions, when setting, tend to create gaps at the bottom and walls of the filling, especially in the dentin areas, due to changes in volume during the setting reaction. Hereby fine gaps are formed between the tooth cavity and the filling, causing a secondary decay (caries), since both food debris and bacteria show a tendency to enter said gaps. Also the pulp may be injured. This phenomenon has been described e.g. in Danish Patent Specification No. 122,259, disclosing a filling and dental adhesive composition based on olefinically unsaturated monomers. The composition comprises monomer (e.g. methacrylic acid methyl ester, powdered polymer and a polymerization catalyst and/or accelerator based on redox systems, preferably peroxides and tertiary amines of sulphurous compounds, and is particularly characterized by further comprising at least one hydroperoxide, preferably n-butyl hydroperoxide. According to Test 3 of said Danish patent, a varnish (primer composition) is prepared as a 10% solution of a film-forming methacrylic acid methylester copolymer containing 0.1% tert.-butyl hydroperoxide in acetone. A primer comprising an α-cyano acrylate monomer containing hydroperoxide may be used instead at the bottom of the cavity before filling. Comparison tests have shown that such a primer composition results in a bonding capacity only half as strong as that of the abovementioned varnish (containing an organic solution of the film-forming polymer).

U.S. Pat. No. 4,240,832 discloses a composition useful in forming a solid cured protective layer assisting healing of the pulp and stimulating the secondary dentin formation. This composition is prepared in the form of a two-paste system, of which one is a polymerized condensate of a phenolic resin with an aldehyde, e.g. a methyl salicylate-formaldehyde resin, and the other component is a paste containing calcium hydroxide. When both components are mixed, a highly viscous composition is formed, containing, if desired, various fillers, and which, when cured, forms a hard capping over an exposed pulp to protect it against the penetration of tissue irritating agents. Thus, a capping or sealing composition is provided, suitable for treating exposed pulp, replacing prior art compositions within this field containing free isoeugenol, which, however, inhibits the polymerization of acrylic monomers.

Further, U.S. Pat. No. 3,785,832 discloses a primer composition or a varnish useful as a coupling agent between dentin and acrylate fillings. Said coupling agent is a reaction product of N-phenyl glycine and a glydicyl ether containing an epoxy group such as p-chlorophenyl-2,3-epoxypropyl ether or a reaction product of bisphenol A and epi-chloro hydrine. This composition is to be dissolved in organic solvents, e.g. acetone, chloroform, and ether.

Finally, Joseph M. Antonucci in J. Dent. Res., Vol. 57 No. 3 (March 1978): "Aldehyde Methacrylate Derived from Hydroxybenzaldehydes", pages 500 to 505, discloses the synthesis of certain aldehyde group-containing methacrylates from the three isomeric hydroxybenzaldehydes to form the three monomeric aldehyde methacrylates. Said methacrylate monomers containing a pending aldehyde group are suggested as coupling agent for application on the interphase between dental filling compositions on acrylate or methacrylate basis and hard tooth tissue such as dentin. For this purpose it has previously been suggested, according to U.S. Pat. No. 3,200,142 to use a surface active comonomer, NPG-GMA, i.e. N-(2-hydroxy-3-methacryloxypropyl)-N-phenylglycine, which primarily reacts with calcium ions in apatite (apatite constitutes the inorganic phase in dentin) so as to form chelate complexes. Treatment with said chelate forming coupling agent provides, according to Antonucci, a distinct albeit modest adhesion promoting effect. Furthermore, Antonucci suggests using coupling agents designed to react primarily with the organic phase of the dentin (which predominantly consists of collagen). These coupling agents comprise methacrylate monomers containing aldehyde groups so as to form Schiff bases with the protein in order to promote the adhesion between dental filling composition and dentin. Said methacrylate monomers containing aldehyde groups may be applied as comonomers in conventional dental filling compositions. Antonucci only indicates this theoretical applicability, but does not describe any real experimental testing in this respect. The reference only contains a brief statement of a preliminary experiment involving the polymerisation of liquid mixtures of ortho, metha and para(2-methacryloxyethoxy)-benzaldehyde which are applied as film coatings on polished bone slabs. Such films are indicated as being resistant to polar solvents, whereas corresponding films applied to glass slides do not adhere to the glass surface any more after a few days treatment with solvents. Antonucci's theoretical explanation for this behaviour is formation of a Schiff base from free aldehyde groups on the bottom side of the copolymer film and free primary amino groups on the dentin surface according to the reaction scheme

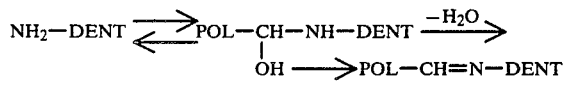

wherein POL designates a polymeric film and DENT designates the dentin surface. According to Antonucci this reaction proceeds similarly to the reaction known from the immobilisation of enzymes by means of polymers derived from vanillinmethacrylate(4-methacryloxy-3-methoxybenzaldehyde). Besides, Antonucci discusses the possibility of formation of certain types of benzoyl radicals during polymerisation, which would give rise to further covalent bonds to dentin by means of a free radical polymerisation. The reaction would imply chain transfer followed by graft polymerisation and/or polymeric coupling reactions, involving hydrogen bonding as well as physical interactions, including reactions between unreacted aldehyde groups and available polar groups in the dentin surface. Furthermore, Antonucci indicates the possibility of oxidation of unreacted aldehyde groups so as to form carboxylic acid groups capable of further enhancing the adhesion by bonding to the apatite-mineral phase. These numerous suggestions about possible reaction mechanisms are not supported by experimental testing. Actually, it has subsequently been found that in practice the Antonucci system does not work as supposed.

When the methacrylic acid ester of parahydroxybenzaldehyde

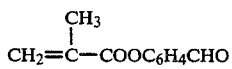

was tested in exactly the same manner as described in the working examples of the present application a very low bonding strength of 0.1 kg/mm² was obtained. The poor results may presumably be attributed to the phenomenon that formation of a Schiff base as theoretically implied by Antonucci in the above reaction mechanism does not represent a stable bonding in an aqueous environment such as the one prevailing in the oral cavity when fillings are applied to freshly drilled and rinsed dentin surfaces.

Apart from the fact that the above prior art primer compositions have rather complicated structures and are quite easily affected by water, they do not provide a desirable and sufficient adhesive bonding strength between dentin and filling, and, which is most important, they will suffer from formation of gaps so that there is a risk of secondary caries (decay) and pulp injuries. Accordingly, the object of the present invention is to eliminate or minimize the said disadvantages of prior art bonding agents by providing a rather simple composition suitable for use in an aqueous environment which gives rise to far better adhesive bonding strengths than prior art compositions in this field.

The present invention relates to a composition consisting essentially of an aldehyde, an olefinically unsaturated monomer, preferably an ester of acrylic or methacrylic acid, containing active hydrogen and, optionally, water and/or a toxicologically acceptable volatile organic solvent. It is possible according to the invention, that aldehyde function, active hydrogen and (meth)acrylic ester groups are part of the same molecule.

The invention also relates to adhesion promoting agents ("liner compositions") for application on collageneous substances, characterized in that they comprise the above composition.

The invention further relates to a process for preparing a composition as defined above by mixing an aldehyde with an olefinically unsaturated monomer, preferably an ester of acrylic or methacrylic acid, containing active hydrogen and, optionally, water and/or a toxicologically acceptable volatile organic solvent.

The present invention finally relates to the use of an agent as defined above to promote adhesion of collageneous material to itself or to a curable composition based on an olefinically unsaturated monomer, preferably between dentin and a dental filling material based on (meth)acrylic acid esters.

The compositions according to the invention give rise to bonding strengths between dentin and conventional acrylate compositions known in dentistry of about 1.8 kg/mm² measured as tensile strength after curing at room temperature (23±1° C.) and following storage in water for 24 hours at 37±1° C.

In comparison, treatment with the compositions disclosed in EP-A 0,058,483 (commercially available under the trade name ®Scotch-bond) provides a tensile strength of only about 0.3 kg/mm².

Aldehydes which may be used in the agent according the the invention are low molecular weight organic compounds (compounds with 1 to 20, preferably 1 to 10 carbon atoms, in particular 2 to 6 carbon atoms) carrying or being able to release at least one aldehyde group so that it is available at the conditions under which the agent is used. The aldehyde group may be situated on an aliphatic, an aromatic or a heterocyclic molecule moiety, and among the investigated aldehydes may for example be mentioned acetic aldehyde, vanilline, salicylic aldehyde, o-phthalic aldehyde, anis aldehyde and furfural, cf. examples 14 to 17 below. Aliphatic mono- and dialdehydes are preferred according to the invention.

Other examples of aldehydes to be used according to the invention are formaldehyde and compounds which are able to release formaldehyde (in particular in aqueous solution), propionaldehyde, butyraldehyde, glutaraldehyde, glyoxal and benzaldehyde.

The second essential compound of the compositions according to the invention are olefinically unsaturated monomers which contain at least one active hydrogen atom. By "active hydrogen" is meant an OH-, NH$_2$-, NH-, SH-, PH- or CH-group such as in alcohols, phenols, carboxylic acids, sulphonic acids, amines, amides, urethanes, ureas, mercaptans, phosphines, malonic acid derivatives and 1,3-diketo compounds. Monomers containing an aliphatic OH-group, an aliphatic or aromatic amino or amido group, a urethane or urea group, are preferred according to the invention. Moreover, preferred monomers are esters of acrylic or methacrylic acid. Optionally the monomers containing active hydrogen may be used as mixtures with monomers which have no active hydrogen atoms.

Examples of suitable monomers with or without active hydrogen include the following:

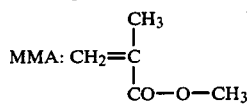   (1)

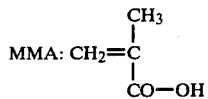   (2)

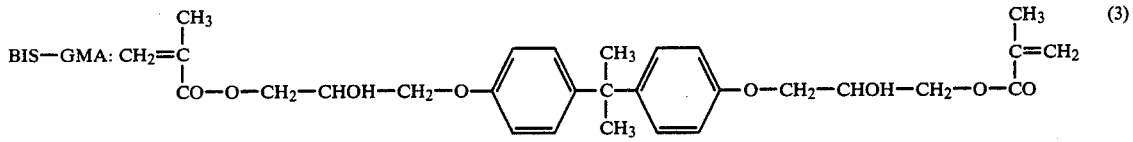   (3)

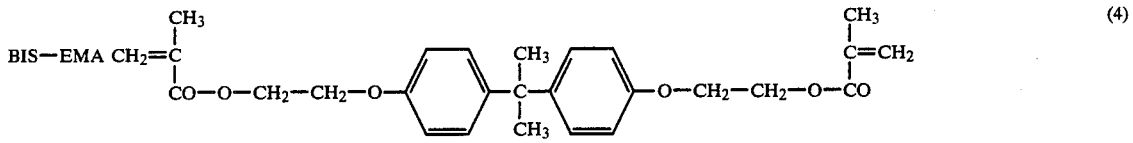   (4)

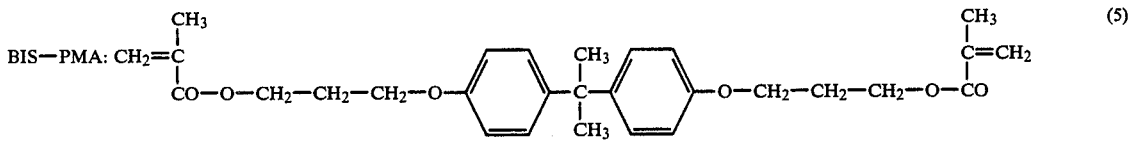   (5)

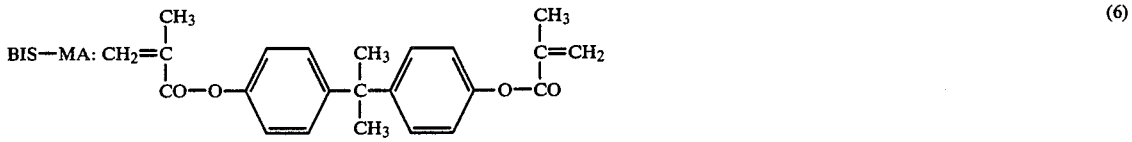   (6)

   (7)

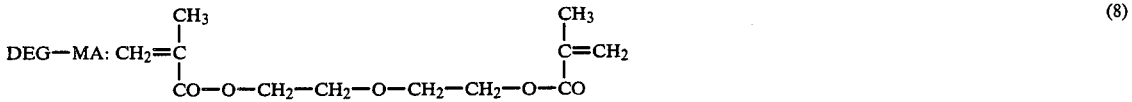   (8)

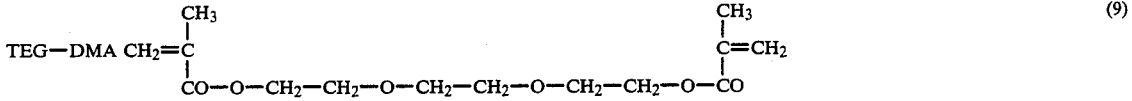   (9)

   (10)

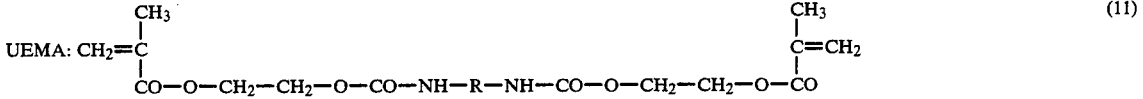   (11)

(R = trimethyl-hexamethylene)

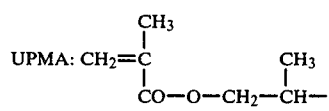
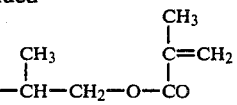

(12)

(R = trimethyl-hexamethylene)

and the corresponding acrylates. Further examples include hydroxyethyl(meth)acrylate, pentaerythritol di- and tri-(meth)acrylate, glycerol di(meth)acrylate, methylvinylalcohol, vinylbenzylalcohol, allyl alcohol, crotylalcohol, cinnamylalcohol, hydroxypropyl(meth)acrylate and (meth)acrylamide.

Of course other conventional olefinic monomers may be used together with the essential components of the compositions according to the invention.

Examples of compounds which contain an aldehyde function, olefinic unsaturation and active hydrogen in one molecule are (meth)acrylates of α-hydroxyaldehydes, such as the reaction product of glycerol aldehyde and methacrylic acid chloride.

An inspection of the above formulae displays that one or two double-bonds form part of each monomer. When one double-bond is present in the molecule the monomer is termed monofunctional and when two double-bonds are present the monomer is termed bifunctional.

The first resin filling compositions available on the market were all based on the monomer MMA, i.e. methylmethacrylate. This resin is termed with the generic name "acrylic resin". However, most modern dental filling compositions contain BIS-GMA, called "Bowenresin".

The monomers (1)-(12) all have one group in common, the methacrylate group MA. Compound (2) is methacrylic acid and compounds (3)-(12) are called modified methacrylates. In formulae (11) and (12) a urethane group —NH—COO— appears: Said compounds are sometimes designated urethane-acrylates.

Among the above methacrylate monomers, Nos. 1, 4, 5, 6, 7, 8, 9 and 10 have no content of active hydrogen, whereas the other monomers contain OH- or NH-groups, and therefore they may be used as monomers with active hydrogen in the agent according to the invention. This is seen from the below comparison experiments where the methacrylate monomers MMA (methylmethacrylate) and TEG-DMA (triethylene glycol dimethacrylate) alone, when tested in the same manner as indicated in the working examples as a mixture with the most preferred aldehyde, i.e. glutaric aldehyde, provide low bonding strengths (average of 0.30 and 0.35 kg/mm², respectively). On the other hand, methacrylate monomers containing active hydrogen such as 2-hydroxyethylmethacrylate, 3-hydroxypropylmethacrylate, methacrylamide, BIS-GMA and UEMA provide high to moderate bonding strengths with average values of 1.9, 1.3, 0.8, 0.9, and 1.2 kg/mm², respectively, together with glutaric aldehyde, cf. Examples 11 to 13 below.

The compositions according to the invention preferably are in liquid form at room temperature. Since some of the aforementioned ingredients are solids, the mixture of aldehyde and olefinic monomer may be dissolved in water and/or a toxicologically acceptable organic solvent which easily evaporates such as acetone or ethanol. Preferably, the compositions according to the invention contain 1 to 50% by weight, particularly 3 to 15% by weight, of the aldehyde and 5 to 80% by weight, particularly 10 to 60% by weight, of the olefinically unsaturated monomer containing active hydrogen, if no compound is being used which contains all three essential functional groups, i.e. active hydrogen, aldehyde and olefinic unsaturation.

The bonding agent according to the invention is different from the coupling system described by Antonucci by comprising a monomer which contains active hydrogen in its molecule. When the agent is applied to collageneous material the aldehyde presumably reacts with secondary amino groups, whereby a structure is formed, which may be represented by the formula R-CHOH-N(A)-collagen. The monomer containing active hydrogen may then be coupled to the above intermediary reaction product with the formation of water. This may be accomplished in aqueous environment such as a wet dentin surface. A possible reaction mechanism is as follows:

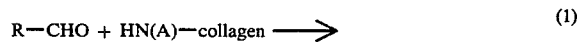

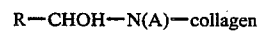

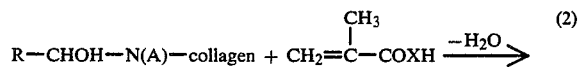

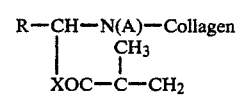

wherein R designates the above aldehyde molecule moiety, which may be aliphatic, aromatic or heterocyclic, X designates the rest of a methacrylate monomer containing active hydrogen, and A is hydrogen or is a bond to a structural moiety in collagen. This proposed mechanism comprises no formation of a Schiff's base as taught by Antonucci, but depends on the presence of an active hydrogen atom in a monomer molecule.

The agent according to the invention comprises inexpensive components being easily commercially available, it exhibits moderate to high bonding strength when applied to the interphase between collagenous material such as drilled cavities in dentin, and curing compositions based on olefinically unsaturated monomers such as dental filling compositions, and it is applicable with great success in an aqueous environment such as freshly rinsed tooth cavities.

The liner composition of the invention enables filling materials to be far better bonded to dentin so that formation of gaps and penetration of microorganisms and dyeing materials is avoided, and besides it minimizes the need for removal of healthy tooth structure in order to make the retention-forming undercuttings. Furthermore, the liner composition may be used in cavities which only partly are located in enamel, e.g. for repairing the neck of a tooth. Furthermore, since it is possible to operate also in an aqueous environment, there is an advantage over the conventional use of reactive monomers for this purpose, containing highly water sensitive components, such as carboxylic acid chlorides and isocyanate groups (cf. E. Asmussen and E. C. Munksgaard: "Bonding of Restorative Resins to Dentin by Means of Methacryloyl Chloride and Methacryloyl-R-Isocyanate", Scand. J. Dent. Res. (1983) 91:153–155).

The liner composition of the invention has been specially examined using a combination of a hydroxyl group containing acrylate monomer, i.e. hydroxy ethyl methacrylate, and various aldehydes, particularly the series of lower aliphatic aldehydes: formaldehyde, acetaldehyde, propionaldehyde, butyraldehyde and glutaraldehyde, among which the lastmentioned has been found particularly suitable.

When, immediately after treatment with the liner composition of the invention, the usual tooth filling compositions are applied containing said acrylate based monomers together with the usual appropriate catalysts, initiators and accelerators, said compositions will react with the freshly applied liner composition, and immediately a crosslinking with the applied filling composition will take place so as to form a strong adhesion between the filling composition and the dentin surface treated with the liner composition.

The above bonding (tensile strength) was examined by usual measuring procedures. Extracted human teeth were used which had been stored in a wet state. The teeth were embedded in epoxy resin by moulding and a flat dentin surface was produced by wet grinding and polishing. The final polishing was performed with carborundum paper No. 1000. Then the surface, if desired, was treated with a chelating agent such as EDTA (0.5 molar solution, pH=7.4) or with 35% phosphoric acid ($H_3PO_4$). The adhesive may e.g. be a 5% aqueous formaldehyde solution combined with β-hydroxyethyl methacrylate (HEMA). The aldehyde solution and HEMA may be applied separately on the dentin surface or, preferably, mixed together and may, besides, be comprised in an aqueous solution in various portions. The formulation of such mixtures is indicated in the following examples. The ground dentin surfaces were treated for about 1 minute with the liner composition and dried with blown air for 5 seconds.

To produce a test sample for measuring the tensile strength, a cylindrical cleaved teflon mold was clamped on the treated dentin surface as described above (cf. O. Zidan, E. Asmussen and K. D. Jørgensen "Correlation between Tensile and Bond Strength of Composite Resins", Scand. J. Dent. Res (1980) 88: 348-351). In most of the tests a thin layer of P-10 enamel adhesive (from 3M Company) was applied to the dentin, before the mold was filled with composite resin, e.g. "Concise Cap-C-Rynge" ® from 3M Company. A round drill no. 016 clamped in the hole of a stand was mounted on the teflon mold and pressed into the still curing composition layer. The arrangement was allowed to stand for 10 minutes at room temperature (23±1° C.). After a period of 24 hours, the sample with drill was mounted in an "Instron" tensile apparatus, and the value of the tensile strength was calculated as the stress applied at rupture divided by the sectional area of the test sample at the fracture. For each set of testing conditions as indicated below in the examples measurements on 5 test samples were performed.

In the comparison test using the liner composition ®Scotchbond (from 3M Company), the instructions of the manufacturer have been exactly followed. The above testing procedure was performed both with pretreatment of the newly polished dentin surfaces by means of EDTA and by rinsing only with pure destilled water. The purpose of the treatment with EDTA is the removal of certain inorganic constituents of dentin so as to leave a surface rich in collagen.

Further, it was found that treatment with $H_3PO_4$ to remove the smearing layer which is a mixture of inorganic particles and organic gel-like substances formed in the drilling procedure (c.f. E. Asmussen's text book "Plastic filling compositions"), resulted in a low bonding strength. The explanation hereof may be protonization of the amino or amido groups of collagen so that these are rendered less reactive towards the aldehyde.

It has, furthermore, been established that a considerably better bonding strength is obtained with the primer (liner) composition of the invention than by the prior technique using as a liner isocyanate group containing acrylate monomers. This is probably due to the sensitivity of the latter to an aqueous environment. Even when carefully dried, some water will still remain in the dentin surface. Another possible explanation of the function of the liner of the invention is that the reaction products of dentin collagen and aldehydes possibly act as a polymerization catalyst (especially in the form of carbonium ions) for the (meth)acrylate monomers.

As to possibe deleterious effects of the aldehydes on the teeth, e.g. by penetrating through the dentin canals to the pulpa, it should be noted that no irritating or toxic effects have occurred. It was found that 5 minutes' application of a 4% formaldehyde solution can be tolerated by the pulpa. It should, furthermore, be noted that glutaraldehyde is used for endodontic purposes, i.e. for treatment of pulpa canals and root treatment. Diffusion through dentin canals in hard dentin amounts to 200 μm only and thus the pulpa of the tooth is only slightly exposed to the aldehyde, and the risk of chemically irritating the gingiva is negligible, too. In surgical heart operations, it is furthermore an accepted practice to use glutaraldehyde fixated heart valves for implantation.

Regarding any effect of the hydroxy group containing acrylate monomers, it should be noted that e.g. HEMA is used for endodontic purposes, and this material in a polymerized state is even for contact lenses, due to its high tissue compatibility.

Although the above description of the invention specifically refers to the use of the liner composition in connection with the repair of teeth, it will be obvious that the liner composition is useful also on other collagenous materials both in living organisms and in unanimate preparations, e.g. in connection with osteosurgery or for glueing materials to e.g. leather and bone. The invention will be further illustrated by the following examples.

EXAMPLE 1

The procedure as set forth above in the general part of the specification was followed using an aqueous formaldehyde solution in the tests A–E and HEMA, which were applied as a mixture in aqueous solution. The results are indicated in the following Table I which shows that without formaldehyde (test A), without HEMA (test B) or without any (test C) only a poor bond strength resulted. However, application of formaldehyde and subsequent application of HEMA provided good bonding. The bonding strength was better using P-10 enamel binder (test E compared to D) as an intermediate layer. Application of formaldehyde and HEMA in the same solution also resulted in a good bond strength (test F-K). The strongest bonds were obtained in the tests G and I. In these tests average bond strengths of 0.6 kg/mm² were obtained. A pretreatment of the dentin with 35% H₃PO₄ (test L), however, resulted only in poor bond strength when compared to pretreatments with 0.5 molar EDTA (tests D-K).

dum paper no. 1000), and the edge region between the filling and the dentin was examined under a microscope. It was found that out of 20 fillings prepared in this way, all but one were free from gaps. This means that the treatment with the liner composition inhibits the poly-

TABLE 1

| Experiment No. | Bond strength between restorative resin and dentin ||||  Bonding strength (kg/mm²) ||
|---|---|---|---|---|---|---|
| | Treatment of dentin |||| | Standard |
| | EDTA | CH₂O* | HEMA** | P-10 E.B. | average | deviation |
| A | + | — | 100 | + | 0.12 | 0.13 |
| B | + | 35 | — | + | 0.07 | 0.08 |
| C | + | — | — | + | 0.09 | 0.10 |
| D | + | 35 | 100 | — | 0.22 | 0.09 |
| E | + | 35 | 100 | + | 0.39 | 0.12 |
| F | + | 18 + 50 || + | 0.35 | 0.14 |
| G | + | 5 + 50 || + | 0.60 | 0.43 |
| H | + | 2 + 50 || + | 0.30 | 0.24 |
| I | + | 7 + 30 || + | 0.57 | 0.34 |
| K | + | 5 + 70 || + | 0.28 | 0.25 |
| L | H₃PO₄ | 18 + 50 || + | 0.05 | 0.05 |
| M | Scotchband ™ |||| 0.29 | 0.11 |

*Concentration in mg per 100 μl solution
**Concentration in μl per 100 μl solution

EXAMPLE 2

The procedure of the introductory part of the specification was followed, cylindrical cavities being produced having a depth of about 1.5 mm and a diameter of about 2.3–6.0 mm. The dentin adhesive (35% HEMA plus 5% glutaraldehyde in aqueous solution) was applied with a brush on the edges and the bottom surface. After 60 seconds the cavity was blown dry, and an acrylate filling composition (Silux ® from 3M Company) was filled into the cavity with subsequent polymerization of means of irradiation with light. The filling composition "Silux" ® is based on the polymeric components BIS-GMA and TEGDMA and contains ®Aerosil as a filler. It was polymerized by irradiation with light through an intense light conductor according to the manufacturer's instructions (30–40 seconds of irradiation, dependent on the depth of the filling). After a residence time of 5–10 minutes in water, excess filling was polished (by means of wet polishing with carborunmerization shrink of the filling material in the marginal region.

The above results show that the previously inevitable and strongly undesirable microscopic gaps formed by shrinkage, are substantially eliminated.

Tensile strength measurements were performed as generally described in the introductory part of the specification. Some of the flat polished dentin surfaces were treated with an aqueous EDTA solution, while the remaining surfaces were treated only by rinsing with pure water. Said surfaces were then covered with an aqueous solution of HEMA and glutaraldehyde in various concentrations. The surface was mounted in a teflon mold with a cylinder, which was filled with the same type of composite resin as indicated above. The tensile strength of the filling to the dentin was measured after a residence time of 24–72 hours in water at 37° C.

The values of the tensile strengths are indicated in table II below.

TABLE II

| No. | % glutaraldehyde[a] | % HEMA[a] | Tensile strength kg/mm² | Standard deviation | Lower higher value | No. of measurements | Notes |
|---|---|---|---|---|---|---|---|
| 1 | 3 | 9 | 0.41 | 0.19 | 0.25–0.62 | 3 | |
| 2 | 3 | 30 | 0.97 | 0.09 | 0.90–1.11 | 5 | |
| 3 | 3 | 50 | 0.81 | 0.28 | 0.52–1.23 | 5 | |
| 4 | 4 | 12 | 0.47 | 0.13 | 0.32–0.60 | 4 | |
| 5 | 5 | 20 | 0.84 | 0.31 | 0.48–1.27 | 5 | |
| 6 | 5 | 30 | 1.68 | 0.64 | 0.76–2.30 | 5 | |
| 7 | 5 | 40 | 1.08 | 0.70 | 0.12–1.94 | 6 | |
| 8 | 7.5 | 20 | 0.45 | 0.30 | 0.15–0.84 | 6 | |
| 9 | 7.5 | 30 | 1.20 | 0.41 | 0.85–1.78 | 6 | [b] |
| 10 | 7.5 | 40 | 1.46 | 0.45 | 1.08–2.09 | 6 | |
| 11 | 10 | 15 | 1.02 | 0.43 | 0.70–1.54 | 4 | |
| 12 | 10 | 30 | 1.23 | 0.56 | 0.61–1.95 | 5 | |
| 13 | 10 | 60 | 0.64 | 0.13 | 0.46–0.80 | 5 | |
| 14 | 15 | 30 | 1.33 | 0.44 | 0.46–1.66 | 6 | |
| 15 | 4 | 35 | 1.78 | 0.53 | 0.91–2.37 | 6 | |
| 16 | 3.5 | 35 | 1.81 | 0.66 | 1.18–2.64 | 6 | |
| 17 | 5 | 35 | 1.82 | 0.18 | 1.62–2.10 | 6 | |
| 18 | 10 | 30 | 1.06 | 0.23 | 0.67–1.26 | 6 | No EDTA pretreatment |
| 19 | 10 | 30 | 0.41 | 0.17 | 0.18–0.63 | 6 | Water rinsing after Aldehyde/HEMA |
| 20 | 15 | 30 | 0.42 | 0.15 | 0.28–0.62 | 6 | No EDTA pretreatment, but aldehyde/HEMA with 1.67 M EDTA added pH 7.4 [b] |
| 21 | 5 | 30 | 0.99 | 0.27 | 0.74–1.41 | 6 | |

TABLE II-continued

| No. | % glutaraldehyde[a] | % HEMA[a] | Tensile strength kg/mm² | Standard deviation | Lower higher value | No. of measurements | Notes |
|---|---|---|---|---|---|---|---|
| 22 | 10 | 30 | 1.98 | 0.57 | 1.72–2.75 | 4 | [c] |
| 23 | 10 | 60 | 0.89 | 0.17 | 0.70–1.06 | 5 | [c] |

[a]Percentage (weight/vol.) in an aqueous mixture of glutaraldehyde and HEMA (hydroxyethyl-methacrylate)
[b]Storage in water at 37° C. for 24 hours before measuring.
[c]Storage in water at 37° C. for 72 hours before measuring.

EXAMPLES 3–7

The procedure of Examples 1 and 2 was followed, but using acetaldehyde, propionaldehyde, butyraldehyde, heptanal and o-phthalic acid aldehydes, respectively, in concentrations of 5% by weight. Results were obtained similar to those of Examples 1 and 2:

| Ex. No. | The liner with aldehyde | Average tensile strength kg/mm² |
|---|---|---|
| 3 | acetaldehyde | 1.0 |
| 4 | propionaldehyde | 1.5 |
| 5 | butyraldehyde | 1.0 |
| 6 | heptanal | 0.1 |
| 7 | o-phthalic acid aldehyde | 0.7 |

EXAMPLE 8

The procedure of Example 2 was repeated, but replacing HEMA by methacryl amide. As the aldehyde component glutaraldehyde was used. An average tensile strength of 1.14±0.8 kg/mm² was obtained.

EXAMPLE 9

The above lining composition has furthermore in a few cases been tested clinically in treatment of a pure dentin surface, i.e. an exposed tooth neck, which was subjected to the usual preparing treatment and then rinsed with EDTA (0.5M, pH 7.5) followed by rinsing with water for 60 seconds and dry blowing with air. Thereafter, a layer of the lining composition was applied as described in Example 2, No. 6, which layer after a period of 60 seconds was carefully blown with air to remove excess material, and then a usual filling composition was used for capping, i.e. the above Silux ®, which thereafter was carefully covered with a thin celluloid strip and subjected to treatment with light according to the manufacturer's instructions (30 seconds) and finally the capping thus provided was polished. No disadvantages such as irritation of pulpa were detected. On inspection (30 days after treatment) the coating applied was found to be fixed satisfactorily on the tooth neck, and no irritation of the gingiva had occurred.

EXAMPLE 10

The grain sides of two pieces of hide were primed with a composition of the invention as specifically described in Example 2, No. 7, i.e. based on glutaraldehyde and HEMA. After one minute the hide surfaces were superficially dry, and the above P-10 Enamel Bond was applied. Thereafter the pretreated surfaces were pressed firmly together. After curing the layers could not be drawn apart without breaking, i.e. the adhesion turned out to be stronger than the substrate itself.

EXAMPLES 11 TO 13

Example 2 was repeated, with different compositions:

| Ex. No. | Aldehyde (Vol %) | Methacrylate (Vol %) | Acetone (Vol %) | Water (Vol %) | Average tensile strength (kg/mm²) |
|---|---|---|---|---|---|
| 11 | glutaric aldehyde 5% | 3-hydroxy-propyl-methacrylate 35% | 0% | 60% | 1.4 |
| 12 | glutaric aldehyde 5% | BISGMA 35% | 45% | 15% | 0.8 |
| 13 | glutaric aldehyde 5% | UEMA 35% | 45% | 15% | 1.3 |

EXAMPLES 14 TO 17

Proceding in the same manner as described in Examples 1 to 7 using HEMA and the aldehydes and concentrations stated below gives the following results:

| Ex. No. | Aldehyde | Vol % | HEMA Vol % | Average tensile strength |
|---|---|---|---|---|
| 14 | Vanillin | 10% | 35% | 0.45 |
| 15 | Salicyl aldehyde | 10% | 60% | 0.4 |
| 16 | Anis aldehyde | 10% | 55% | 0.25 |
| 17 | Furfural | 10% | 35% | 0.25 |

EXAMPLE 18

The process was as described in Examples 1 and 2 with test pieces of pig's bones, 1×1×0.3 cm and with a bonding agent of glutaric aldehyde/HEMA as stated in Table II No. 17. The average tensile strength was determined as 1.18±0.27 kg/mm².

We claim:

1. In the adhesion of dental fillings and elements to substructures by applying an adhesion composition to the filling material and/or substructure and then a material to be adhered to the substructure, the improvement wherein the adhesive composition comprises an aliphatic aldehyde containing 1 to 20 carbon atoms and an ester of acrylic or methacrylic acid containing on —OH, —NH₂ or NH-moiety.

2. The process according to claim 1, wherein the adhesive composition includes a solvent.

3. The process according to claim 1, wherein the aldehyde is selected from the group consisting of formaldehyde, a compound which is able to release formaldehyde, acetaldehyde, propionaldehyde, butyraldehyde and glutaraldehyde.

4. The process according to claim 1, wherein the aldehyde is glutaraldehyde and the ester is hydroxyethyl methacrylate.

5. The process according to claim 1, wherein the substructure is a drilled tooth and the material to be adhered thereto is a tooth-filling composition.

6. The process according to claim 5, wherein the tooth-filling composition is acrylate or methacrylate based.

* * * * *

UNITED STATES PATENT AND TRADEMARK OFFICE
CERTIFICATE OF CORRECTION

PATENT NO. : 4,593,054
DATED : June 3, 1986
INVENTOR(S) : Erik Asmussen et al.

It is certified that error appears in the above—identified patent and that said Letters Patent is hereby corrected as shown below:

Title Page, "Inventors", lines 1,2 — Delete "Christian Munksgaard" and substitute --Erik Chr. Munksgaard--

Col. 11, last line of Table I — Delete "TM" and substitute --®--

Col. 11, line 35 — Before "means" delete "of" and substitute --by--

Col. 12, Table II, line 11 under "Lower higher value" — Delete "0.70-1.54" and substitute --0.60-1.54--

Signed and Sealed this

Sixteenth Day of September 1986

[SEAL]

Attest:

DONALD J. QUIGG

Attesting Officer

Commissioner of Patents and Trademarks